United States Patent [19]

Westley

[11] 3,944,573

[45] Mar. 16, 1976

[54] ISO-LASALOCID A

[75] Inventor: John Westley, Mountain Lakes, N.J.

[73] Assignee: Hoffman-La Roche Inc., Nutley, N.J.

[22] Filed: Apr. 2, 1974

[21] Appl. No.: 457,298

[52] U.S. Cl............................... 260/347.3; 424/285
[51] Int. Cl.² ........................................ C07D 307/12
[58] Field of Search ................................. 260/347.3

[56] References Cited
UNITED STATES PATENTS 3,702,333    11/1972    Nakanishi et al. ............... 260/347.8

Primary Examiner—Harry I. Moatz
Attorney, Agent, or Firm—Samuel L. Welt; Bernard S. Leon; Frank P. Hoffman

[57] ABSTRACT

Iso-lasalocid (an isomer of lasalocid A) is produced by a species of Streptomyces. The isomer, its halogen derivatives and its salts exhibit antibacterial and antiprotozoal activity and are useful as antibacterial and antiprotozoal agents.

2 Claims, No Drawings

ISO-LASALOCID A

BRIEF DESCRIPTION OF THE INVENTION

This invention relates to a new antibiotic and to methods for its production by fermentation, its isolation and its use as an antibacterial and antiprotozoal agent.

The microorganism producing the antibiotic useful in this invention is a Streptomyces organism isolated from a sample of soil collected at Hyde Park, Massachusetts. Lyophilized tubes of the culture bearing the laboratory designation X-537 were deposited with the U.S. Department of Agriculture, Agricultural Research Service, Northern Utilization Research and Development Division, Peoria, Ill. The culture, given identification number NRRL 3382 by the Agricultural Research Service, has been made available to the public through NRRL.

The antibiotic material, heretofore identified as antibiotic X-537A (Lasalocid A), upon laboratory analysis has been found to be 6- 7(R)-[5(S)-ethyl-5- (5(R)-ethyltetrahydro-5-hydroxy-6(S)-methyl-2H-pyran-2(R)-yl) tetrahydro-3(S)-methyl-2(S)-furyl]-4(S)-hydroxy-3(R),5(S)-dimethyl-6-oxononyl -2,3-cresotic acid, i.e., a compound of the formula:

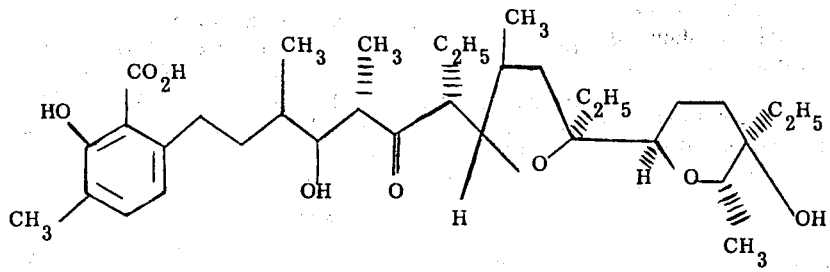

As indicated above, the present invention relates to an isomer of antibiotic Lasalocid A its derivatives and its pharmaceutically acceptable salts. The specific isomer to which the invention relates is a compound of the formula:

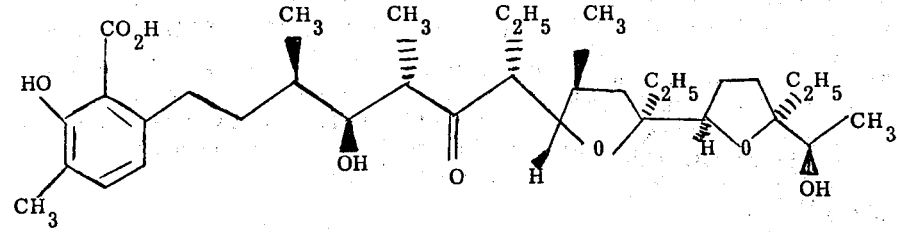

having the name: 6-[7(R)-[5(S)-ethyl-5-(5(S)-ethyl-tehahydro-5-(1(R)-hydroxyethyl)-furan-2(R)-yl)-tetrahydro-3(S)-methyl-2(S)-furyl[-4(S)-hydroxy-3(R),5(S)-dimethyl-6-oxononyl]-2,3-cresotic acid.

The isomer is prepared by the fermentation of a suitable medium with Streptomyces X-537 under aerobic submerged conditions, with the pH of the frementation broth adjusted to about neutral, i.e., about 6.5 to 7.5. The medium utilized contains a nitrogen source, such as yeast, a yeast derived product, corn meal, bean meal and the like, with soybean meal being the most preferred; salts such as potassium phosphate, calcium carbonate, and trace elements; a carbohydrate source, such as sugar, molasses and the like, with starch being the most preferred; and a vegetable or animal fat or oil such as soybean oil or lard oil to provide carbon source and foam control. The fermentation is carried out at slightly elevated temperatures, i.e., between about 25° and 35°C., with the preferred incubation temperature being about 31°C. After an incubation of about 4 to 9 days, the fermentation broth is filtered and the antibiotic recovered by extraction.

After the fermentation is complete, a variety of procedures can be employed for the isolation and purification of the isomer. Suitable isolation and purification procedures includes solvent extraction techniques, such as batchwise extraction or counter-current continuous flow liquid-liquid extraction columns and gel permeation chromatography in a non-aqueous system.

The pharmaceutically acceptable salts of the isomer can be prepared by conventional means. These salts are prepared from the free acid form of the antibiotic or its derivatives by methods well known in the art, for example, by washing the free acid in solution with a suitable base or salt. Examples of such pharmaceutically acceptable basic substances capable of forming salts for the purpose of the present invention include alkali metal bases such as sodium hydroxide, potassium hydroxide, lithium hydroxide and the like; alkaline earth metal bases such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

The halogen derivatives of Iso-lasalocid A are compounds of the formula:

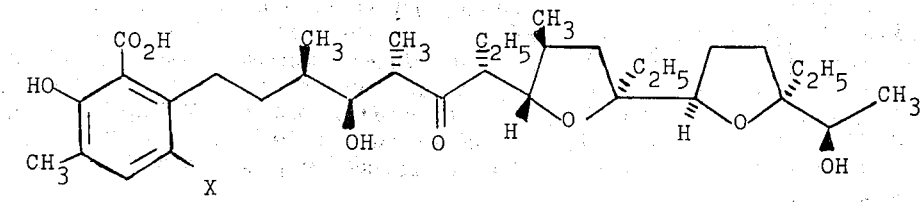

wherein X is selected from the group consisting of chlorine, bromine and iodine.

Among the many procedures suitable for production of the halogen derivatives of Iso-lasalocid A there may be included bromination utilizing bromine, chlorination utilizing chlorine or iodination utilizing iodine monchloride and the like.

The relative antibiotic activity of the Iso-lasalocid A in in vitro testing against a number of gram positive bacteria was calculated by comparing pure antibiotic lasalocid A and Iso-lasalocid A using the cup-plate agar diffusion technique. The calculated values of the Iso-lasalocid A were based on an activity of 100 for lasalocid A and are shown in the table below.

| Organism | Percentage relative activity of Iso-lasalocid A based on lasalocid A = 100 |
| --- | --- |
| Mycobacterium phlei | 0.4 – 2 |
| Staphylococcus aureus | 3 – 11 |
| Sarcina lutea | 10 – 30 |
| Bacillus sp. TA | 13 – 50 |
| Bacillus sp. E | 40 – 100 |
| Bacillus subtilis | 75 |
| Bacillus simplex | 100 |

Iso-lasalocid A is active orally in rats ($CD_{50}$=34 mg/kg) against Entamoeba histolytica and subcutaneously in mice ($CD_{50}$=268 mcg/kg) against a local infection of Trichomonas vaginalis.

The nature and objects of the present invention can be more fully understood by making reference to the following examples.

EXAMPLE 1

Preparation of Iso-lasalocid A

The streptomyces organism was grown in aerated submerged culture in the shaken flasks. The pH of the broth was adjusted by the addition of KOH solution to 6.5–7.5, then the broth was sterilized. A tank fermentation was used herein, a 5–10% inoculum consisting of 3-day-old submerged growth from aerated bottles was used in the tank. The medium contained 2% yellow split peas, 1% cornstarch, 0.1% $K_2HPO_4$ and 2% lard oil. The fermentation was carried out at 28°C under positive air pressure, with air-flows of 5–10 cu. ft. of air per minute per 40- to 80-gallon liquid charge. The broth was harvested after 6 days fermentation, filtered, and the antibiotic was recovered by extraction. The extraction was carried out as follows:

204 Liters of broth were filtered and the wet filter cake was suspended in 100 liters of ethyl actate and the mixture was stirred overnight at room temperature. The mixture was then filtered and the water layer was separated and discarded. The ethyl acetate solution, assaying 30 million Bacillus E units, was concentrated in vacuo to 3 liters, washed with 10% sodium carbonate solution, and dried with anhydrous sodium sulfate.

On further concentration to 300 ml and dilution with 350 ml of petroleum ether (B.P. 50–60°C), 41 g of solid material, assaying 25 million Bacillus E. units, separated. This solid material was then extracted in a Soxhlet apparatus with 4 liters petroleum ether (B.P. 50–60°C) for 40 hours. The extract was taken to dryness in vacuo, the crystalline residue suspended in petroleum ether and filtered. Iso-lasalocid A is found in the filtrate.

EXAMPLE 2

Isolation of Iso-lasalocid A

A portion of the concentrated filtrate from the large scale preparation of Example 1 was chromatographed on a 200 tube (each 80 ml capacity) countercurrent distribution apparatus. The sample was dissolved in 160 ml of the mixed phases (heptane-ethyl acetate-methanol-water, 27:18 18:2) and the solution placed in the first two tubes. After 380 transfers, the following tubes were pooled and the solids recovered after the evaporation contained:

A. Mixture of lasalocid homolgs B, C, D and E
B. Lasalocid A
C. Crude Iso-lasalocid A Fraction C, which was in crude form and contained sodium and potassium as salts, was dissolved in methylene chloride and washed with 0.1 N HCL to convert it to the purified Iso-lasalocid A free acid.

The Iso-lasalocid A which was isolated had a melting point of 183°–185°C.

EXAMPLE 3

Preparation of the Sodium Salt of Iso-lasalocid A

Approximately 100 mg. of Iso-lasalocid A was dissolved in methylene chloride and treated with a saturated solution of sodium carbonate. The solvent layer was concentrated with hexane to give 104 mg. of the crystalline Iso-lasalocid sodium salt (m.p. 183°–183.5°C).

EXAMPLE 4

Preparation of the Potassium Salt of Iso-lasalocid A

Approximately 387 mg. of Iso-lasalocid A was dissolved in 200 ml of ethyl acetate and treated with 0.2 N KOH. The solvent layer was dried over $K_2CO_3$ and concentrated under vacuum to a colorless foam weighing approximately 360 mg.

EXAMPLE 5

Preparation of the Barium Salt of Iso-lasalocid A

Approximately 0.77 g of Iso-lasalocid A was dissolved in methylene chloride and heated with a saturated solution of Ba(OH)$_2$. The solvent layer was separated and concentrated under vacuum to a foam weighing approximately 0.62 g.

EXAMPLE 6

Preparation of the Bromine Derivative of Iso-lasalocid A

To a solution of 3,672 g of the sodium salt of Iso-lasalocid A in 500 ml. of methylene chloride at 3°C was added slowly, over a period of 1 hours, 0.323 ml of bromine in 50 ml of methylene chloride. After 1 hour, the solution was allowed to slowly warm up to 15°C and 1 liter of water was added. The solvent layer was removed, washed in turn with aqueous sodium bisulfite, aqueous sodium carbonate and water. The solution was dried over $Na_2SO_4$ and concentrated to an oil from which 2.1 g of crystals were recovered after addition of acetone/hexane. The crystalline material was dissolved in methylene chloride and washed with 1 N HCl. The solvent layer was concentrated to a small volume and after addition of acetone/hexane, the brominated Iso-lasalocid A was recrystallized from aqueous methanol.

The brominated Iso-lasalocid A had a melting point of 185°–186°C.

The relative antibiotic activity of the bromo derivative in vitro testing against Bacillus TA was calculated by comparing a pure antibiotic lasalocid A and the bromo derivative of Iso-lasalocid A using the cup-plate agar diffusion technique. The bromo derivative had a percent relative in vitro activity of 75.

I claim:

1. A compound of the formula:

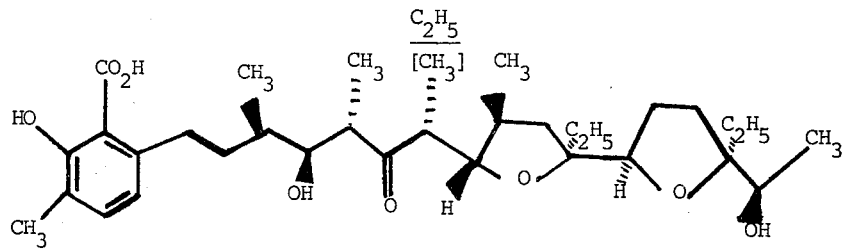

or the pharmaceutically acceptable salts thereof.

2. A compound of the formula

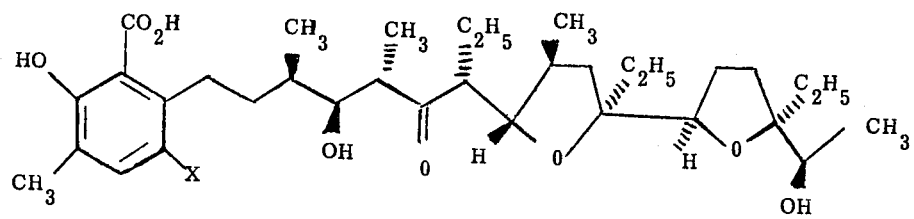

wherein X is selected from the group consisting of chlorine, bromine and iodine, or the pharmaceutically acceptable salts thereof.

* * * * *

UNITED STATES PATENT AND TRADEMARK OFFICE
CERTIFICATE OF CORRECTION

PATENT NO. : 3,944,573
DATED : 3/16/76
INVENTOR(S) : John Westley

It is certified that error appears in the above-identified patent and that said Letters Patent are hereby corrected as shown below:

In claim 1, the formula

" 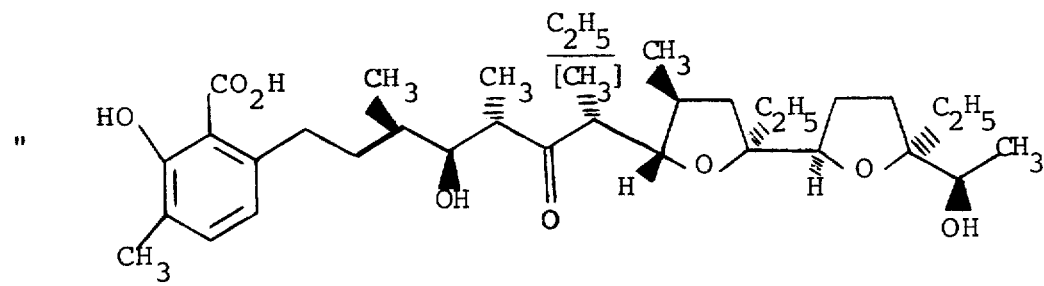 "

Should be

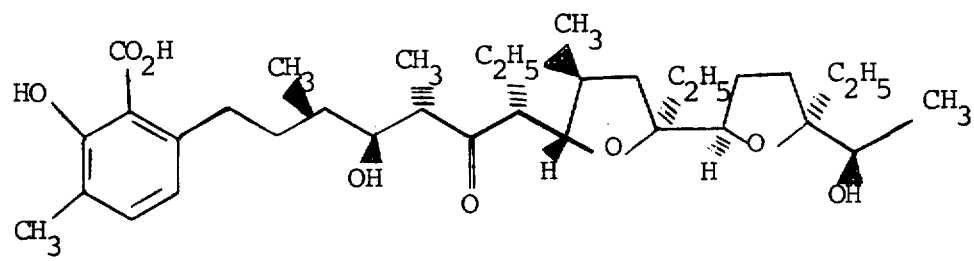

Signed and Sealed this

Thirteenth Day of July 1976

[SEAL]

Attest:

RUTH C. MASON
*Attesting Officer*

C. MARSHALL DANN
*Commissioner of Patents and Trademarks*